United States Patent
Tepper et al.

(10) Patent No.: US 6,660,176 B2
(45) Date of Patent: Dec. 9, 2003

(54) MOLECULAR IMPRINTING OF SMALL PARTICLES, AND PRODUCTION OF SMALL PARTICLES FROM SOLID STATE REACTANTS

(75) Inventors: Gary Tepper, Glen Allen, VA (US); Dmitry Pestov, Richmond, VA (US); Natalia Levit, Richmond, VA (US); Gary Wnek, Midlothian, VA (US)

(73) Assignee: Virginia Commonwealth University, Richmond, VA (US)

( * ) Notice: Subject to any disclaimer, the term of this patent is extended or adjusted under 35 U.S.C. 154(b) by 7 days.

(21) Appl. No.: 10/054,708

(22) Filed: Jan. 24, 2002

(65) Prior Publication Data

US 2002/0102312 A1 Aug. 1, 2002

Related U.S. Application Data

(60) Provisional application No. 60/263,524, filed on Jan. 24, 2001, provisional application No. 60/289,515, filed on May 9, 2001, and provisional application No. 60/316,265, filed on Sep. 4, 2001.

(51) Int. Cl.[7] .............................. C08F 2/48; C08J 9/26; G01N 30/48; G01N 33/53
(52) U.S. Cl. ........................ 216/56; 427/243; 427/244; 427/508; 436/518; 436/531; 521/61
(58) Field of Search ........................... 216/56; 210/656; 252/408.1; 427/508, 243, 244; 436/518, 531; 521/61

(56) References Cited

U.S. PATENT DOCUMENTS

| | | | | |
|---|---|---|---|---|
| 5,587,273 A | * | 12/1996 | Yan et al. ............... | 430/269 |
| 5,630,978 A | * | 5/1997 | Domb ..................... | 264/330 |
| 5,885,837 A | * | 3/1999 | Winkler et al. .......... | 435/91.1 |
| 5,959,050 A | * | 9/1999 | Mosbach et al. ......... | 526/201 |
| 6,051,372 A | * | 4/2000 | Bayerl et al. ............ | 435/4 |
| 6,080,387 A | * | 6/2000 | Zhou et al. .............. | 424/45 |
| 6,177,513 B1 | * | 1/2001 | Takeuchi et al. ......... | 525/54.1 |

FOREIGN PATENT DOCUMENTS

WO    WO 01/19886 a1    *    3/2001

OTHER PUBLICATIONS

Smothers, Wm. K. et al "Photopolymers for holography" SPIE, vol. 1212 Practical Holography, pp 20–29, Jan. 1990.*

* cited by examiner

Primary Examiner—Anita Alanko
(74) Attorney, Agent, or Firm—Whitham, Curtis & Christofferson, P.C.

(57) ABSTRACT

Small particles of polymeric material are produced by expansion of a mixture of monomers and a propellant. The size and shape of the particles can be precisely tailored by materials selection and expansion conditions. Particles of 10 nanometers to 100 microns can be produced. If monomers exhibiting solid state reactivity are utilized, the particles thus formed can be polymerized at any time after formation. The particles produced by this method can be molecularly imprinted by incorporating a template into the particle prior to fully curing the particle, in a manner which allows selective extraction of the template from the cured particle after formation without deformation of the imprint site. A two step polymerization process allows the particles to be deposited on and adhered to a wide variety of substrates without additional agents. The molecularly imprinted particles can be used in a wide variety of applications including the selective binding of analyte from a sample, where the analyte is the same as the template or is of substantially the same size and has a similar arrangement of chemical functional groups. Imprinted molecularly imprinted particles can be used for targeted delivery of agents in biological applications. Non-imprinted particles formed by the expansion technique using monomers of solid state reactivity can be used in optical data storage systems.

54 Claims, 5 Drawing Sheets

MOLECULAR IMPRINTING OF SMALL PARTICLES, AND PRODUCTION OF SMALL PARTICLES FROM SOLID STATE REACTANTS

This appl. claims benefit of prov. Nos. 60/263,524 filed Jan. 24, 2001, 60/289,515 filed May. 9, 2001 and 60/316,265 filed Sep. 4, 2001.

BACKGROUND OF THE INVENTION

1. Field of the Invention

The invention pertains to molecular imprinting of small particles and, more particularly, to a method of molecular imprinting which utilizes a propellant as the solvent and dispersing agent of the matrix material and to imprinted particles formed by the method as well as devices coated with imprinted particles, such as, for example, surface acoustic wave (SAW) devices. In addition, the invention pertains to a method for the formation of small particles of monomers containing solid-state reactivity.

2. Description of the Prior Art

Molecular imprinting is a process, which involves arranging of polymerizable functional monomers around a template (print) molecule. This is achieved either by utilizing non-covalent interactions such as hydrogen bonds, ion-pair interactions, etc. (non-covalent imprinting), or by reversible covalent interactions (covalent imprinting) between the print molecule and the functional monomers. Typically, a molecule to be imprinted (template) is combined with a mixture of functionalized and non-functionalized monomers so that the monomers surround the template. In the process, functionalized monomers align themselves in a binding relationship to complementary functional groups on the template to form therefore a complex with the template. After polymerization, functional groups are held in position by the highly cross-linked polymeric matrix. The template is then removed, and the resulting material contains imprinted binding sites which are complimentary in size and shape to the template. The complementary binding groups, arising from the functionalized polymer groups incorporated during the imprinting, are specifically positioned to enhance the preferential substrate binding and, if desired, subsequent catalysis. The imprinted polymer materials are capable of specific sorption or specific catalytic activity. A good description of state of the art of molecular imprinting can be found in Mosbach, K., Trends in Biochemical Sciences, Vol. 7, pp. 92–96, 1994; Wulff, G., Trends in Biotechnology, Vol. 11, pp. 85–87, 1993; and Andersson, et al., Molecular Interactions in Bioseparations (Ngo. T. T. ed.), pp. 383–394.

The functionalized monomers usually used for molecular imprinting are: acrylic acids [Anderson, L.; Sellergren, B; Mosbach, K Tetrahedron Lett. 1984, 25, p.5211. Sellergren, B.; Lepisto, M.; Mosbach, K. J. Am. Chem. Soc. 1988, 110, p.5853. Andersson, L. I.; Mosbach, K. J. Chromatogr. 1990, 516, p.313. Matsui, J.; Miyoshi, Y.; Takeuchi, T. Chem. Lett. 1995, p.1007.], vinylbenzoic acids [Andersson, L.; Sellergren, B.; Mosbach, K. Tetrahedron Lett. 1984, 25, p.5211], acrylamino-sulfonic acids [Dunkin, 1. R.; Lenfeld, J.; Sherrington, D. C. Polymer 1993, 34, p.77], amino-metacrylamides [Beach, J. V.; Shea, K. J. J. Am. Chem. Soc. 1994, 116, p.379.], vinylpyridines [Ramstrom, O.; Andersson, L. I.; Mosbach, K. J. Org Chem. 1993, 58, p.7562. Kempe, M.; Fischer, L.; Mosbach, K. J. Mol. Recognit. 1993, 6, p.25], vinyl imidozales [Kempe, M.; Fischer, L.; Mosbach, K. J. Mol. Recognit. 1993, Vol. 6, p.25. Leonhardt, A.; Mosbach, K. React. Polym. 1987, 6, p.285.], acrylamides [Yu, C.; Mosbach, K. J. Org Chem. 1997, 62, p.4057.], and vinyl-iminodiacetic acids [Dhal, P. K.; Arnold, F. H. J. Am. Chem. Soc. 1991, 113, p.7417. Kempe, M.; Glad, M.; Mosbach, K. J. Mol. Recognit 1995, 8, p.35.].

Prior to this invention, methods of molecular imprinting have achieved only modest success in the enhancing polymer selectivity and catalytic activity. The reason for this is, that in order to be effective in a wide scale, imprinted materials must have binding/active sites to be homogeneous (in specificity and activity), be well formed (based on shape and reactivity), and be easily accessible by the reactant molecules (access is affected by shape, size and polarity of the channels leading to the catalytic site). The imprinted polymeric materials created by prior art methodologies have sites that are generally not very accessible and not homogenous, as they often have different binding affinities and/or reactivities. These problems mainly arise from the method used for producing the imprinted polymer particles.

A common method of molecular imprinting is referred to as solution polymerization. This method results in the formation of imprinted sites that are completely encased within the polymer. In order to enable an access to those sites, the polymer monolith must be subjected to mechanically grinding to produce particles that have exposed sites. Grinding produces irregularly shaped particles and typically only less than 50 percent (50%) of the ground polymer is recovered as useable particles with size less than 25 $\mu$m. Irregular particles generally give less efficient devices mainly because of the deformation of a large number of the binding sites. As a result, damage to the sites adversely affects their selectivity and activity. An alternative method to increase accessibility to the imprinted sites is by the use of porogen compounds which are known to generate foam-like polymer structures when combined with polymer forming materials. Porogens, which are typically inert solvents, are mixed with the polymerizable monomers during the imprinting process and are washed away after polymerization is complete. This creates large pores that allow access to the created binding sites. However, while the porogens are removed, some of the structural integrity of the polymer can be lost at the same time, leading to the deformation of the sites and loss in specificity and activity.

Another alternative for molecular imprinting is by direct polymerization of particles in liquid media. Surfactants are used to create molecular microstructures, such as micelles or reverse micelles. Then, inorganic or organic monomers are polymerized around those molecular microstructures at the surfactant-solvent interface to form polymer beads, dispersed in the liquid media to prevent agglomeration. The size and shape of the formed beads highly depend on the chemistry of the mixture and reaction conditions, such as temperature and stirring. When the surfactant is removed, the remaining material has a size and shape complementary to the size and shape of the initial molecular microstructures. By controlling variables such as surfactant selection and concentration, a variety of different microstructure shapes such as micellar, cubic, tetragonal, lamellar, tubular and reverse micellar can be formed. Consequently, monodisperse particles of a variety of different sizes and porous materials with a variety of different shapes of pores and channels can be created. Methods of making porous material are described, for example, in the following patents each of which are incorporated herein by reference: U.S. Pat. No. 5,250,282 to Kresge et al; U.S. Pat. No. 5,304,363 to Beck et al; U.S. Pat. No. 5,321,102 to Loy et al; U.S. Pat. No. 5,538,710 to Guo et al; U.S. Pat. No. 5,622,684 to Pennavaia et al; U.S. Pat. No. 5,750,085 to Yamada.

Molecular imprinting by direct polymerization of particles in liquid media is more advantageous, but still has limitations due to the liquid media needed to disperse particles to prevent particles agglomeration. Therefore, after polymerization, particles need to be separated from the liquid media for further use, which is not an easy task, especially for small particles. While in many applications, imprinted polymers should be deposited on the special surfaces, such as in chemical and biological sensors, and in chromatography and filtration devices. Deposition of the imprinted polymer material and adherence on the surface remains a big problem.

U.S. Pat. No. 5,587,273 to Yan et al., which is herein incorporated by reference, describes a way of molecular imprinting of polymer film directly on the surface of sensor. The invention describes molecularly imprinted substrate and sensors employing the imprinted substrate for detecting the presence or absence of analytes. One embodiment of the invention comprises first forming a solution comprising a solvent and (a) a polymeric material capable of undergoing an addition reaction with a nitrene, (b) a crosslinking agent (c) a functionalizing monomer and (d) an imprinting molecule. A silicon wafer is then spin coated with the solution. The solvent is evaporated to form a film on the silicon wafer. The film is exposed to an energy source to crosslink the substrate, and the imprinting molecule is then extracted from the film. Described method is an advance in deposition of imprinted polymers to the sensing surfaces. But there is no solution disclosed in the literature for imprinting of polymer particles directly on the surfaces of devices. Prior researchers have focussed on the preparation of imprinted particles, but not on attachment of the particles to the surfaces of device, and it would be advantageous to have a methodology which allowed direct attachment of imprinted particles to substrate surfaces.

Aerosol and vapor technology has been used for many industrial and medicinal applications which utilize particles. An aerosol is a two-phase system consisting of a gaseous continuous phase and a discontinuous phase of individual particles. The individual particles in an aerosol can be solids or liquids (Swift, D. L. (1985), "Aerosol characterization and generation," in Aerosols in Medicine Principles, Diagnosis and Therapy (Moren, F. et al. eds) 53–75). Supercritical fluids have been used in the production of aerosols for precipitation of fine solid particles. The phenomenon was first observed and documented as early as 1879 and was described the precipitation of solids from supercritical fluids (Hannay, J. B. and Hogarth, J., On the Solubility of Solids in Gases, Proc. Roy. Soc. London, 1879, A29, 324). The sudden reduction in pressure reduces the solvent power of the supercritical fluid, causing precipitation of the solute as fine particles. This phenomenon has been exploited in many processes for producing fine particles, using co-solvents (Sievers, et al. PCT Publication WO 9317665 published Sep. 16, 1993, Donsi, G. and Reverchon, E. (1991), "Micronization by Means of Supercritical Fluids: Possibility of Application to Pharmaceutical Field," Pharm. Acta Helv. 66:170–173), anti-solvents (Debenedetti, P. G., et al. (1993), "Application of supercritical fluids for the production of sustained delivery devices," J. Controlled Release 24:27–44, PCT Publication WO 90/03782 of The Upjohn Company for "Finely Divided Solid Crystalline Powders via Precipitation Into an Anti-Solvent", Yeo, S-D, et al. (1993), "Formation of Microparticulate Protein Powders Using a Supercritical Fluid Antisolvent," Biotechnology and Bioengineering 41:341–346), as well as pure supercritical solvents (Mohamed, R. S., et al. (1988), "Solids Formation After the Expansion of Supercritical Mixtures," in Supercritical Fluid Science and Technology, Johnston, K. P. and Penninger, J. M. L., eds., Tom, J. W. and Debenedetti, P. B. (1991), "Particle Formation with Supercritical Fluids—a Review," J. Aerosol. Sci. 22:555–584, Smith U.S. Pat. No. 4,582,731 for "Supercritical Fluid Molecular Spray Film Deposition and Powder Formation," issued Apr. 15, 1986, and Smith U.S. Pat. No. 4,734,451 for "Supercritical Fluid Molecular Spray Thin Films and Fine Powders). In the processes described, fine aerosols comprising the desired substance are formed by mixing a nongaseous pressurized or/and supercritical fluid(s) with the desired substance, which is present in a solution, dispersion, suspension, micellar system or emulsion. During rapid reduction of the pressure on composition the pressurized/supercritical fluids form a gas and a gas-borne dispersion of fine particles, liquid or solid.

There are many acronyms associated with those processes, including RESS, GAS or SAS, SEDS, ASES, and PGSS (Jennifer Jung, Michel Perrut Particle design using supercritical fluids: Literature and patent survey Journal of Supercritical Fluids 20 (2001) 179–219). RESS refers to Rapid Expansion of Supercritical Solutions. This process contemplates dissolving the product in the fluid and rapidly depressurizing this solution through a nozzle, causing an extremely rapid nucleation of the product into a highly dispersed material. GAS or SAS is Gas (or Supercritical fluid) Anti-Solvent, one specific implementation being SEDS (Solution Enhanced Dispersion by Supercritical Fluids). The general concept contemplates decreasing the solvent power of a polar liquid solvent in which the substrate is dissolved, by saturating it with carbon dioxide in supercritical conditions, causing substrate precipitation or re-crystallization. ASES is used when micro- or nano-particles are expected. The process contemplates pulverizing a solution of the substrate(s) in an organic solvent into a vessel swept by a supercritical fluid. SEDS is a specific implementation of ASES wherein there is co-pulverizing of the substrate(s) solution and a stream of supercritical carbon dioxide through nozzles. PGSS stands for Particles from Gas-Saturated Solutions (or Suspensions). The process includes dissolving a supercritical fluid into a liquid substrate, or a solution of the substrate(s) in a solvent, or a suspension of the substrate(s) in a solvent followed by a rapid depressurization of this mixture through a nozzle causing the formation of solid particles or liquid droplets.

Development of microspheres/capsules, containing a load of needed ingredient, is one of the most rapidly developing area in medicine, food industry, agrochemicals, cosmetics. Many efficient drugs have been reformulated to allow control of delivery location and rate, the active substance being distributed directly to the target to enhance the treatment efficiency and reduce the doses and related side effects. Some of the researchers classify particles/capsules smaller than 1 $\mu$m as nanoparticles and those larger than 1000 $\mu$m as macro-particles. Commercial particles/capsules typically have a diameter between 3 and 800 $\mu$m and contain 10–90 wt. % of carrier material. A wide range of materials have been embedded/encapsulated in microspheres/capsules, including adhesives, agrochemicals, live cells, active enzymes (W. Fischer, B. Muller, Patent EP 0 322 687, Dec. 17, 1988; P. Debenedetti, J. W. Tom, S. D. Yeo, G. B. Lim, Application of Supercritical Fluids for the Production of Sustained Delivery Devices. Journal of Controlled Release, 24, 1993, 27–44; L. Frederiksen, K. Anton, B. J. Barrat, P. Van Hoogevest, H. Leuenberger. Proceedings of the 3 rd International Symposium on Supercritical Fluids; Tome 3; G. Brunner, M. Perrut (Eds.), ISBN 2-905-267-23-8, 17–19

October, Strasbourg, 1994, 235–240; M. Hanna, P. York, Patent WO 95/01221, 1994; M. Hanna, P. York, Patent WO 96/00610, 1995; K. Mishima, S. Yamaguchi, H. Umemoto, Patent JP 8-104830, 1996; P. Pallado, L. Benedetti, L. Callegaro, Patent WO 96/29998, 1996; W. Majewski, M. Perrut, Patent FR 99.12005, 27 September). Despite these advances, there are few materials which include an active agent embedded or encapsulated in a carrier matrix (or otherwise associated with the matrix) which are specifically designed for targeted delivery of the active agent to a particular site. It would be advantageous for example, if a material were available where a drug or toxin were associated with a slow release matrix material, wherein the material could be targeted for delivery to a tissue, organ or other site of activity, and then have slow sustained release at the targeted site. Prior to this invention, no such delivery material having each of these attributes existed.

There are several method of handling materials with solid state reactivity to develop small particles of reacted solid materials. There is a need to produce small particles which retain reactivity in the solid state. Reprecipitation in liquid solvents is one of the techniques used (Application: JP 92-238160 19920907 to Kasai; Oikawa H; Oshikiri T; Kasai H; Okada S; Tripathy SK; Nakanishi H. Various types of polydiacetylene microcrystals fabricated by reprecipitation technique and some applications. POLYMERS FOR ADVANCED TECHNOLOGIES 2000, Vol 11, Iss 8–12, pp 783–790). The process is carried out by dissolving an organic material in a solvent, adding poor solvent, followed by crystallization or polymerization of the microcrystals to form particles. Adding 4-BCMU in EtOH solvents to water dropwise and irradiating with high-pressure Hg lamp gave polydiacetylene particles showing average diameter 100–200 nm. The reprecipitation method is a useful technique to fabricate organic microcrystals such as polydiacetylene (PDA), low-molecular-weight aromatic compounds, organic functional dyes that have features located in a mesoscopic phase between a single molecule and bulk crystals, and organic microcrystals which are expected to exhibit peculiar optical and electronic properties.

One known variation involves recrystallization in supercritical fluid by change of temperature and addition of anti solvents (Kasai, Hitoshi; Okazaki, Susumu; Okada, Shuji; Oikawa, Hidetoshi; Adschiri, Tadafumi; Arai, Kunio; Nakanishi, Hachiro. Fabrication of organic microcrystals by supercritical fluid crystallization method and their optical properties. MCLC S&T, Sect. B: Nonlinear Opt. (2000), 24(1–2), 83–88; Komai, Y; Kasai, H; Hirakoso, H; Hakuta, Y; Okada, S; Oikawa, H; Adschiri, T; Inomata, H; Arai, K; Nakanishi, H. Section 3: Thin Films - Size and Form Control of Titanylphthalocyanine Microcrystals by Supercritical Fluid Crystallization Method. Molecular Crystals and Liquid Crystals, 1998, v.322, p.167, 6p). This method involves the use of solvents which makes the particles thus produced only accessible in or subject to the solvent as an impurity. It would be advantageous to have particles and particle producing methods where both agglomeration and solvent impurities are completely avoided.

SUMMARY OF THE INVENTION

It is an object of the invention to provide an improved method of fabricating molecularly imprinted polymeric particles which can selectively bind specific compounds or classes of compounds.

It is another object of the invention to provide polymeric particles which are molecularly imprinted, and which are capable of substantially improved performance over prior art materials made by different methodologies.

It is yet another object of the invention to provide devices which are used for highly selective binding of molecules or classes of molecules, which are coated with molecularly imprinted polymeric materials, such as for example SAW devices and other sensors, chromatography devices and filters, and purification devices of all types (e.g., cigarette filters, water filters, etc.).

It is still another object of the invention to provide a new and improved method of making micron and less than micron sized particles from compounds that have solid-state reactivity, with or without molecular imprinting.

According to the invention, particles are created from a mixture of propellant and desired substance which is present in the form of solution, dispersion, suspension, micellar system or emulsion; which comprises at least one polymerizable monomer. A "propellant" is a compressed gas or mixture under elevated pressure, where at least one of the components of the mixture may be a supercritical fluid, and, while expanded, propellant dispenses the contents of the mixture to form particles. The term "particle" as used herein refers to both solid particles and liquid droplets. As the mixture passes through a capillary nozzle or other orifice, the mixture undergoes fast expansion so as to create fine particles of the mixture, containing monomer, that are preferably less than 100 microns in size, and most preferably less than 50 microns in size. In one embodiment, the particles include polymerizable monomers with or without cross-linking agents, and an initiating species (e.g., activators which initiate polymerization or cross-linking (or both processes)). In another embodiment, the monomers themselves exhibit solid-state reactivity, meaning that they change from a solid monomer to a solid polymer without a change of the material physical state. This second embodiment can be used to make particles of substantially uniform, small size, which can be molecularly imprinted or not be molecularly imprinted, and constitutes a new manner of handling materials with solid state reactivity. These particles are advantageous in that they are not agglomerated, and do not require a solvent. In addition, they are stable for long periods of time (e.g., 1–10 years) and can be selectively polymerized at any desired time. The particles formed from solid state reactivity monomers can have wide ranging applications including in the formation of coatings on surfaces and in optical data storage.

For molecular imprinting, in either embodiment, a template can be combined with the mixture either before expansion or after particle formation. A template is used for imprinting the polymeric material, and can be any molecule which is selectively releasable from a polymer formed from the monomers in the particle. In many applications, it is preferable that the template does not covalently bond to the polymer which is formed. However, in some applications, the template may be released by hydrolyzing bonds or changing the ionic attraction between a template molecule and the polymer matrix. In molecular imprinting, the template needs to be extracted from the polymer particle after polymerization of the monomer or monomer mixture in the particle formed by expansion. The template can be a chemical or biological compound or substrate (a portion of a biological or chemical compound, or a biological entity). The choice of template will depend on the application planned for the molecularly imprinted polymer particle. Specifically, the template may be a compound (e.g., toxin, carcinogen, or any compound of interest, etc.) that one would like to sense in a gaseous or fluid environment, or a compound which is to be removed from a gaseous or fluid environment by selective binding to the molecular imprint site such as by a filter or other separation device. The invention may also have application in biology or biotechnology. In some cases antigens or enzymes of interest could serve as the template molecule, and then the imprinted polymer particles would be able to selectively bind the specific biological entities. Otherwise, the molecular imprinting can produce the artificial enzymes and antibodies.

However, it should be understood that the imprint can be designed to selectively bind, sorb, or otherwise associate with more than a single compound, which served as the template compound. Specifically, the imprinting process may allow the molecularly imprinted polymer particle to bind any molecule that has a size (spatial size) and/or arrangement of chemical functional groups which is substantially the same as said template. This should be especially useful in the preparation of imprinted polymer particles that may be used, for example, in detection or sorption of chemical and biological warfare agents. Specifically, compounds, which have a size and arrangement of chemical functional groups that are similar to nerve gas agents, or other chemical weapons, but which are not themselves potent substances, may be used to molecularly imprint polymer materials that can then be used to bind, sorb or otherwise associate with the dangerous substances. In this way, the molecularly imprinted materials might be fabricated in a manner which would be more safe than working with the dangerous substances themselves.

If the template is added to the mixture prior to expansion, the distribution of the imprinted sites within the polymer particles is virtually assured. This is because the propellant will solubilize and/or disperse both the matrix forming compounds (i.e. the monomers) and the template to form a homogenous mixture, and after the expansion the particles are formed that contain matrix compounds and template evenly dispersed therein.

If the template is added to the mixture after expansion, the template must be diffused into the particles. This can be done in either the gas or liquid phase using a suitable carrier. Even distribution of the imprinted sites on the surface of the polymer particles may be achieved using this technique because particles are formed with substantially uniform surface representation. The imprinted sites are readily accessible, as the particles surfaces are exposed to the analyte.

The propellant in the mixture being expanded can be 20–99.99% by weight of the entire mixture to be expanded. The mixture, containing at least one monomer, be they monomers having a solid state reactivity, or a mixture of monomers, crosslinkers and initiators, can be 80–0.01% by weight of the entire mixture. If the template is added to the mixture to be expanded, the template can comprise 1–30.00% by weight of the mixture.

This is the first time it has been shown that propellant can be effectively used as a solvent or distribution agent in the formation of molecular imprinting in micron and submicron sized particles. In particular, it is the first time that a propellant has been used for development of micron and submicron sized particles from materials with solid state reactivity. The propellant is maintained in a fluid state under pressure, but, when pressure is relieved, it instantly transitions to a gaseous state. This allows the propellant to be immediately separated from the monomers that will ultimately form the polymer particle not containing impurities due to the propellant. The propellant may advantageously be a supercritical fluid or may include as at least one component a supercritical fluid. The supercritical fluid can solubilize the monomers in the mixture which is to be expanded, and then, after expansion, will leave the particles thus formed as a gas. Examples of propellants which can be used in the practice of this invention include, but not limited to, chlorofluorocarbons (freons), hydrofluorocarbons, alkanes, alkenes, noble gases (e.g., helium and argon), nitrogen, sulfur hexafluoride, fluorocarbons, nitrous oxide, hydrogen, ammonia, carbon monoxide and carbon dioxide.

The ratio of the propellant and monomers in the mixture to be expanded can be adjusted to achieve the formation of particles of varying sizes. Likewise, the nozzle opening can be adjusted to control particle size. The choice of system pressure and temperature can be experimentally optimized and depends on the type of materials to be expanded, monomers, and propellant. The propellant could also be a mixture of more than one material. For example, two different gases might be used, or a supercritical fluid and another compound might be used.

A particularly advantageous aspect of this invention is to produce the molecularly imprinted particles or simply the small particles formed from materials of solid-state reactivity. Particles formed by expansion of a mixture containing propellant and solid state reactivity monomers will not agglomerate, and will be free of solvent, and are stable for long periods of time (1–10 years). These particles can be polymerized into solid particles without a change in the physical state of the material. Thus, these particles may deposited onto surfaces where desired (e.g., on sensors, optical devices), at a desired time, and be selectively polymerized at any time after formation of the particle.

A two step polymerization can be performed in one embodiment of this invention which is particularly advantageous for securing imprinted or non-imprinted particles directly on the surface of a substrate. In the first step, a stream of particles emanating at the site of expansion is subjected to an energy source sufficient to cause an initial polymerization of the monomer while particles are in flight towards a deposition surface or other collection location. This can be performed by radiant energy, such as ultraviolet, gamma radiation, infrared radiation, intense light in the visible spectrum, etc. Alternatively, heat can be used for specific monomers. The purpose of the initial polymerization is to allow some of the polymerization or crosslinking to begin. It is preferable that the initial polymerization is sufficient to make the particles more viscous such that there physical morphology begins to be established. The amount of energy applied will depend on the materials in the composite particle containing monomers and template, the size of the particle, whether or not initiators are present in the particle, the time of flight, and other factors. In the second step, the particles (which are now partially polymerized particles containing template material) are deposited onto a surface of the support, such as a SAW device, chromatography support, or filter, where they are subjected to more energy (e.g., heat or radiant energy) to fully polymerize the particle matrix directly on the surface of the support. This allows the particle to mechanically and/or chemically adhere to the surface of the support without having significant changes in its morphology of the particle. Specifically, the outer surface is fairly solidified in the initial polymerization, however, upon deposition onto a support, a portion of the particle containing monomers would then be polymerizable in the final polymerization step. This monomeric portion may also be selected to chemically interact with functional groups on the support surface. Alternatively, the impact onto the support surface will wedge some of the monomers into cavities and depressions on the surface, whereupon the final polymerization step will assure a mechanical bond of the polymer particle within these cavities and depressions on the surface of the support. Thus, the polymeric particles of this invention are chemically or mechanically attached to the substrate without using an adhering agent or requiring a separate step to achieve good adherence. At the same time the method enables uniform distribution of particles on the support surface.

Alternatively, the particles could simply be collected in a collection container and subjected to the energy sufficient to fully polymerize or "cure" the particles.

The procedure assures that the imprinted small particles of substantially uniform size are formed. The invented procedures of molecular imprinting of polymer particles avoid deformation of the imprint sites by excluding grinding and solvent separation, enables uniform distribution of the imprinted sites, and increases their accessibility to analyte. After formation of the polymeric particles, the template compound is extracted by exposing the polymer particles to excess propellant/other supercritical fluid, or by any other means suitable for displacing the template from the polymeric particle.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
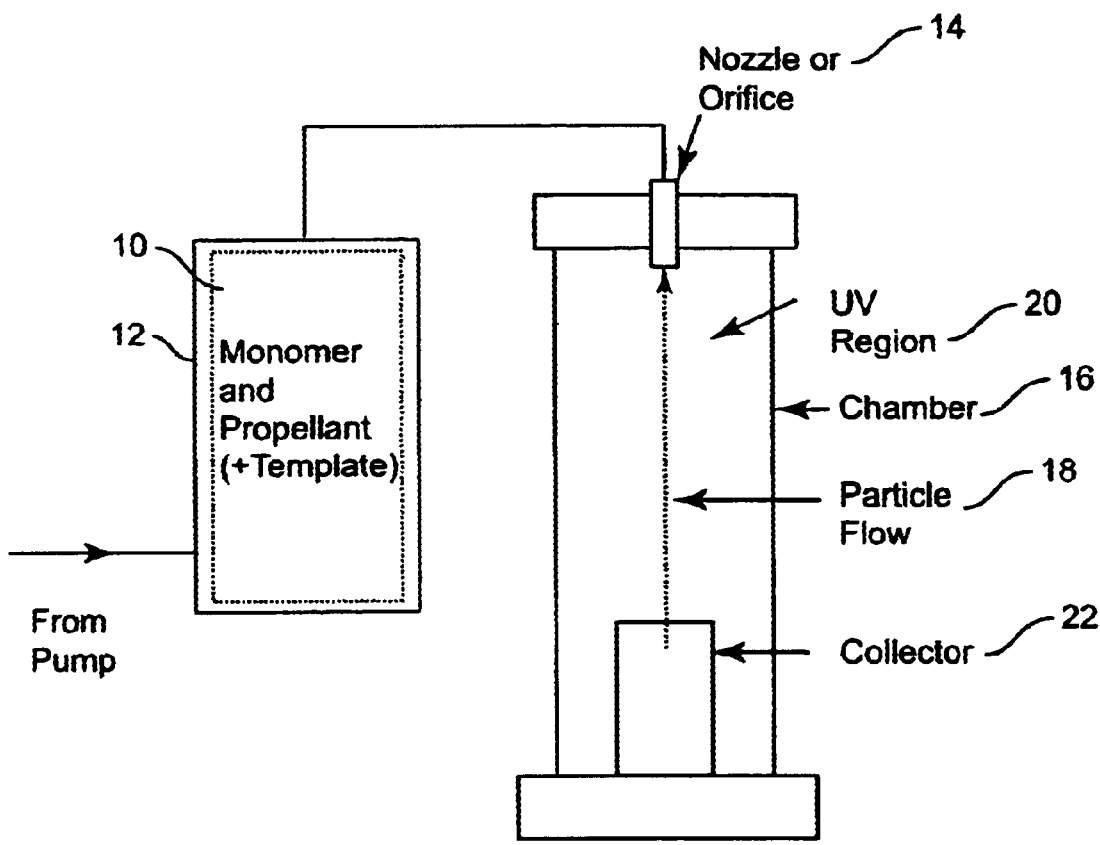
FIG. 1 is a schematic view of an apparatus used for making micron and sub-micron particles, and which is the preferred apparatus configuration for making molecularly imprinted particles according to this invention.

With reference to FIG. 1, in the practice of this invention, a mixture 10 containing at least one monomer and propellant is prepared. This mixture 10 can be prepared in a tank 12 or other storage device, or can be simply the intersection of a plurality of feed lines (not shown) for monomer, propellant, and template.

The "monomers" which can be used in the practice of this invention, are wide ranging. In one type of mixture, the monomers can include a mixture of one or more of the following: functional monomers, cross-linking agents, and initiators which initiate polymerization (e.g., photoinitiators). Examples of functional monomers include acrylic acids, acrylamides, vinylbenzoic acids, acrylaminosulfonic acids, amino-metacrylamides, vinylpyridines, vinylimidazoles, vinyl-iminodiacetic acids, etc. The monomers that can be used in the practice of this invention can be of the variety that undergo polymerization reaction by any known mechanism, such as, cross-linking, polycondensation, or additive polymerization, as well as combination of above.

A wide variety of different crosslinkers may be used in the practice of this invention, including, but not limited to, ethylene glycol dimethacrylate (radical initiation), trimethylolpropane trimethacrylate (radical initiation), divinylbenzene (radical initiation), silane based crosslinkers (initiated by water), etc.

Initiators or other agents, which initiate polymerization and can be used in the practice are also wide ranging. In many applications, a photo-initiator will be advantageously employed. For example, light, UV energy, or some other source of radiant energy can be used to selectively activate the photo-initiator, which will then cause polymerization of the monomers to occur.

In one embodiment of this invention, monomers with a reactivity in the solid state are used to prepare small particles of less than 100 microns, and most preferably particles of a uniform small size less than 50 microns in diameter (in some applications particles having diameters ranging from 10 nm to 1 micron in size can be prepared). The solid state reactivity of specific organic and inorganic molecules has been known since 1916. Reactant materials of solid state reactivity, including solid state polymerization, can be low and high molecular weight substances (polymers, oligomers, monomers) with different physical properties. One embodiment of this invention involves small particles from materials exhibiting solid state reactivity that can then undergo solid state chemical reaction in order to form materials with desired properties, including those with properties different from the bulk material due to size reduction. Recently, small particles/microcrystals from materials with solid state reactivity have attracted much of attention due to the possible unique changes of properties due to the material size reduction. Examples of materials with known solid state reactivity include vinyl stearate (reaction initiated by gamma ray or electron beam), vinyl acetate (reaction initiated by gamma ray), isoprene (reaction initiated by gamma ray), vinyl octacecyl ether (reaction initiated by gamma ray), methacrylic acid (reaction initiated by ultraviolet (UV) or gamma radiation), trioxane (reaction initiated by ring opening of $BF_3(C_2H_5)_2O$), diacetylenes (reaction initiated by heat or UV light), and diolefinic compounds, containing two double bonds, such as, 2,5-distrylpyrazine (DSP) (reaction initiated by UV, gamma rays, and visible light), 2,2'-(2,2-p-phenylene-divinyl)-bis-pyridine (reaction initiated by UV light), diethyl p-phenylenediacrylate (reaction initiated by UV light), dimethyl p-phenylenediacrylate (reaction initiated by UV light). The common formula of diacetylenes is as follows:

Common Formula

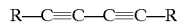

Where the examples of R can be:

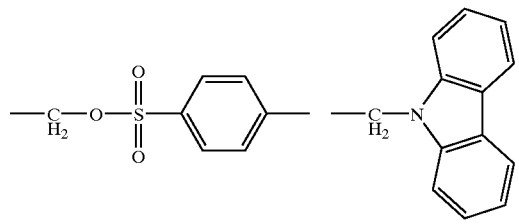

-continued $$-(\underset{H_2}{C})_4-O-\underset{\underset{O}{\|}}{C}-\underset{\underset{H}{|}}{N}-CH_2-\underset{\underset{O}{\|}}{C}-O-C_2H_9$$

The common formula of diolefinic compounds is:

A═══X═══B where,
A—is an atom or chemical group
B—is an atom or chemical group
X—is a chemical group.

An important feature of this invention is that fine aerosols comprising the desired substance are formed by mixing a propellant with the desired substance, which can be present in a different state, such as, a solution, dispersion, suspension, micellar system or emulsion. The propellant may contain co-solvent, surfactants, antisolvents, and other chemical constituents. In a preferred embodiment, the propellant may include, for example, chlorofluorocarbons (freons), hydrofluorocarbons, alkanes, alkenes, noble gases (e.g., helium and argon), hydrogen, fluorocarbons, nitrous oxide, ammonia, carbon monoxide and carbon dioxide. At least one of the components of the propellant can be supercritical fluid. Supercritical fluids are generally gases at atmospheric pressure, but above their critical pressure and temperature assume a liquid-like density and solvent power, combined with the advantages of gas-like viscosity and compressibility. During rapid reduction of the pressure on mixture 10 by discharge through a nozzle or orifice 14 into a chamber 16, at least one of the components of the propellant forms a gas and a gas-borne dispersion of fine particles from the desired mixture (a particle flow 18) is discharged in chamber 16. The formed particles can be both liquid or solid. The chief requirement is that a uniform distribution of monomers and, template if included, is achieved with the propellant, and upon discharge through a nozzle 14, the propellant leaves its association in the mixture in a gas form to produce a particle flow 18 in chamber 16. The propellant can be vented from the chamber 16, or, it can be captured and recycled from the chamber 16 to the tank 12 using a pump.

An important feature of this invention is that monomers can be solubilized in propellant to make mixtures capable of expansion by discharge through a nozzle or orifice 14 into a chamber 16. In this way, the propellant is used to make a mixture 10 that can be segregated into many particles that are emanating from the nozzle or orifice 14. The propellant may contain co-solvent, surfactants, antisolvents, and other chemical constituents. In a preferred embodiment, the propellant may include, for example, chlorofluorocarbons (freons), hydrofluorocarbons, alkanes, alkenes, noble gases (e.g., helium and argon), hydrogen, fluorocarbons, nitrous oxide, ammonia, carbon monoxide and carbon dioxide. Supercritical fluids are generally gases at atmospheric pressure, but above their critical pressure and temperature assume a liquid-like density and solvent power, combined with the advantages of gas-like viscosity and compressibility. The propellant in this invention could contain at least one supercritical fluid, alone or in combination with a gas or other liquid. In addition, the propellant could include other materials, which will solubilize monomers used in the practice of this invention. The chief requirement is that a uniform distribution of monomers and, template, if included, is achieved with the propellant, and upon discharge through a nozzle 14, the propellant leaves its association in the mixture in a gas form to produce a particle flow 18 in chamber 16. Specifically, as the mixture 10 is expanded through the nozzle due to entry of the mixture into a lower pressure environment, all of the gaseous components immediately leave the mixture, leaving only the non-gaseous matrix forming components in the form of small particles. The propellant can be vented from the chamber 16, or, it can be captured and recycled from the chamber 16 to the tank 12 using a pump.

This technique of particle formation, particularly, when supercritical fluids are utilized in the propellant, is based on the tremendous solubility change that occurs during the sudden decompression of a supercritical solution containing a nonvolatile solute by means of an expansion device, such as an orifice or capillary nozzle. The high supersaturation during fluid expansion results in the nucleation and growth of solute particles with mean size ranging from nanometers to tens of microns. The size and morphology of precipitates is controlled by tuning the supercritical solution parameters (concentration of solute, pre-expansion temperature and pressure) as well as the geometry of the expansion device.

The propellant may comprise 20–99.99% by weight of the mixture, and the monomers and other constituents may comprise 80–0.01% by weight of the mixture. In applications of this invention, the template molecule can be added to the mixture 10 in tank 12, or can be added to the chamber 14 for diffusion into the particle flow 16. If added to the mixture 10, the template molecule can comprise 1–30% by weight of the mixture. The size of the particles in the particle flow can be controlled by adjusting the ratio of propellant in the mixture, by choice of nozzle or orifice 14, and by the choice of monomers used in the matrix. The choice of system pressure and temperature are experimentally optimized and depends on the type of materials to be expanded, monomers, and propellant. In certain applications of this invention, particles smaller than 1 micron in size, which are imprinted with a template, can be produced.

In molecular imprinting, the template can be a chemical or biological compound or substrate (a portion of a biological or chemical compound, or a biological entity). Chemical compounds having a molecular weight ranging from 10 to 1,000,000 can be used in the practice of this invention. The choice of chemical compounds is wide ranging and can include, carbohydrates, halogenated compounds, alcohols, ethers, esters, amines, aldehydes, ketones, carboxylic acids, amides, oligosaccharides, polysaccharides, antigens, transition state analog (chemically stable compound and structurally is very similar to the transition state formed during an enzymatic conversion of compound being catalyzed) steroids, nucleotides, nucleosides, oligonucleotides, polyanions, drugs, toxic industrial materials, chemical warfare agents, or chemical agent simulants, insecticides, pesticides, and fungicides. The template can be selected from drugs such as antioxidants, chemotherapeutic agents, steroids, hormones, antibiotics, antiviral agents, antifungals, antiproliferative agents, and antihistamines. Examples of proteins which could be used as templates include nutrient protein, a storage protein, a contractile or motile protein, a structural protein, a defense protein, regulatory proteins (e.g., enzymes). Examples of chemical warfare agents which may act as templates include nerve agents, such as Sarin (GB), Soman (GD), Tabun (GA), GF, TGD, VX; blister agents, such as mustard (HD), lewisite (L), HN-1, HN-2, and HN-3; and agent mixtures, such as HL and HT. Examples of chemical agent simulants which may be used as templates include methyl salicylate, dimethyl methyl-phosphonate, and diethyl malonate, diphenyl chlorophosphate, 2-chlorethyl phenylsulfide, and O-ethyl-S-ethyl phenylphosphonothioate. Examples of substrates which may be used as a template in the practice of this invention include cells (living or nonliving), DNA, proteins, enzymes, viruses, bacteria, nucleic acids, peptides, vitamins, drugs, pollen, and mold.

The template used for molecular imprinting will often be the analyte that is intended to be bound by imprinted polymer. For example, in preparing a chromatography device or filter, the molecularly imprinted polymeric particles of this invention might be intended to bind a particular enzyme or insecticide in a solution under test (i.e., the enzyme or insecticide is the analyte in the chromatographic separation or filtration). In these cases, the template used to prepare the molecularly imprinted polymeric particles often will be the enzyme or insecticide. However, in some situations, will be advantageous to have the template and analyte be different from one another. This allows using more useful or less hazardous templates instead of uncomfortable ones to prepare a molecularly imprinted polymer sensitive to, for example, a hazardous analyte. In this situation, there is a need to have a similarity between the template and analyte in molecular structure, such as geometric size and shape and/or location functional groups. This is described in U.S. Pat. No. 5,801,221 to Tanaka, which is herein incorporated by reference, where it is explained that a template is the target molecule or a structural analog of the target molecule. Examples can be found in the scientific literature, describing cases where an analyte, different from the template, exhibited greater affinity to the template-imprinted polymer [Dickert F. L. et al, Molecularly imprinted sensor layers for the detection of polycyclic aromatic hydrocarbons in water, *Anal. Chem.* 1999, 71 (20), 4559–4563]. This was believed to be due to the changes of cavities followed by the removal of the template. We show in the Examples below that heptane-imprinted DSP and EPA polymers exhibited higher affinity to the smaller in size molecules, such as hexane and pentane, as well as to the template molecule—heptane. This same concept can be extended to more hazardous materials as described above.

The configuration shown in FIG. 1 is designed to provide sufficient energy for an initial polymerization of the particles in the particle flow 18. During this stage, the monomers begin to polymerize and the particles become more viscous. This can be accomplished by having the particles pass through a region where they are exposed to an energy source sufficient to initiate polymerization. FIG. 1 shows this as UV region 20, however, it should be understood that other forms of radiant energy could be applied in the top portion of the chamber 16, including gamma radiation, electron beam, visible light, and X-rays. Furthermore, heat energy could be applied. The type of energy input for the initial polymerization will depend on the monomer materials being polymerized. Finally, a second polymerization, fully polymerizes or "cures" the particles when they reach the collector 22. Examples of collectors include flasks, tubes, filter surfaces, the surface of a SAW device, etc. Again, this second polymerization is accomplished using a source of energy such as heat or radiant energy. The chamber 16 could be filled with air or an inert gas, such as nitrogen, but also could include only the propellant used in the mixture 10.

The two part polymerization process is especially useful when the particles are to be adhered to the surface of a support, such as a sensor or other device. In the initial polymerization, the particles are "formed" and partially solidified with the template in place. This creates the particle with the template to be imprinted. The second polymerization affixes the particle to a device surface. This is accomplished either by having functional groups of the monomers in the particle chemically bond with functional groups on the support surface, and/or by having the monomers at the base of the particle which rests on the substrate surface penetrate into depressions in the surface of the support, and polymerize therein to form a mechanical bond with the substrate. This method of particles polymerization on the surface of device is a significant advance over other molecular imprinting techniques.

First, the surface of a support is uniformly coated with particles, due to the propellant-driven particle stream 18. Second, the molecular imprinting is not subject to distortion or deformation (i.e., the imprinted sites for bonding with analyte are undisturbed). Third, there no additional bonding compounds are needed to affix the imprinted particles to the surface (this avoids material changes to the particles, avoids extra steps in production of sensors and other devices, and avoids faults in the performance of devices due to the bonding compound interference with the real signal, detected upon bonding of analyte to the imprinted particles). Another important advantage of the described technique is the patterned deposition of imprinted polymer particles over the surface of device, such as a biological or chemical sensor, by simple use of a temporary mask covering specific areas to be left uncoated. In this way, imprinted particles can be adhered only to desired surface areas.

The surfaces on which deposition of particles (which are molecularly imprinted or not imprinted) can be a wide variety of materials. They may be conductive, non-conductive, semiconductive (e.g., silicon or gallium arsenide), piezoelectric, magnetic or non-magnetic, quartz, glass, metal, polymer, ceramic, zinc oxide, lithium neobate, etc. In addition, the substrate could be porous or non-porous. For example, in a filter, the fibrils of the filter could be coated with molecularly imprinted polymer particles such that a medium being filtered (e.g., water) could pass through the fibrils, and analytes in the medium could bind at any number of molecularly imprinted particles.

After the particles are cured, the template is removed. This can be accomplished by exposing the particles to excess propellant or other agents which can displace the template from the site of imprinting in the polymer particle. Supercritical fluid also can be used for template extraction. If the template is bonded to the polymer by chemical bonds, ionic attraction, etc. the chemical bonds can be cleaved by any suitable technique (e.g., hydrolysis). In many applications, it will be advantageous to use a template which does not form covalent bonds with the monomers used to create the polymer particle. This makes extraction proceed by less disruptive measures such as simple displacement.

While FIG. 1 shows a system whereby polymerization occurs in two steps, it should be understood that polymerization can occur in a single-step polymerization. For example, if molecularly imprinted particles are desired, which are not to be attached to a substrate surface, one might simply polymerize the particles fully as they emerge from the nozzle 14 and collect them in collector 22.

The preferred embodiment for molecular imprinting of particles can be summarized as a three step process set forth below:

Step 1

Form a mixture containing at least one monomer able to undergo the polymerization or cross-linking and the propellant (20–99.99 wt %) under elevated pressure, at least exceeding atmospheric. The given mixture is then subjected to fast expansion by lowering the pressure to result in formation of small particles in a size range of 10 nm–50 μm containing all the non-gaseous components of the mixture. Such expansion can be achieved by either the passage through the local narrow short orifice or long capillary, or by fast changing the vessel volume.

An obligatory component for molecular imprinting is the introduction of the template to the particles. Template can be present initially as one of the mixture components in this step 1 and therefore, is included in the particle after the particles formation. Otherwise the template is added after the particle formation by a diffusion of the template either from the gas or from the liquid phase.

In the case where the monomer has solid-state reactivity, the highly crystalline monomer can go through an amorphous state due to the fast expansion and/or due to the presence of other polymer components preventing crystallization. Then, there is a transition of the monomer from amorphous to a crystalline state during molecular imprinting. The transition from the amorphous to the crystalline state can be achieved by the exposure to the chemical or by temperature change.

Step 2

Polymerize at least the monomer part of the particle composition by any suitable methodology (e.g., polymerization, cross-linking, or polycondensation) in the presence of the template without a physical distortion of the particle morphology.

Step 3

Remove the template from the particles by the evaporation, dissolving, or extraction without a distortion of particle morphologies. The template can be evaporated from the particles by purging with inert gas having smaller molecules than the template molecule over the particles. Removal of the template also can be achieved by exposing imprinted particles to a liquid, subcritical or supercritical solvent that selectively extract only the template with or without additional heat.

As discussed above, the particles produced by the molecular imprinting method show higher affinity to an analyte which is the same or similar to the template in size and structure (configuration of functional groups) than those particles of similar composition without the introduction of template. Examples 1 and 2 show the preparation of molecularly imprinted DSP and EPA particles according to this invention. These examples demonstrate that the molecularly imprinted particles are selective for analytes of interest, and can be used as to separate, filter, analyze, purify, or otherwise act on an analyte of interest. Furthermore, as discussed above, Examples 1 and 2 demonstrate that the template can be used to produce particles which selectively bind analytes which are not identical (note the selectivity for n-hexane when n-heptane was used as the template). What is required, is to have size (spatial size) and/or structural similarity (note that DSP and EPA particles molecularly imprinted with n-heptane were not selective for iso-octane—while iso-octane has the same number of carbon atoms, but is not of the same spatial size and it does not have a similar structure of chemical functional groups).

This invention also has application in making very thin, patterned or unpatterned coatings on substrate surfaces. The methods used in Examples 1, 2 and 5 illustrate methodologies whereby uniform thickness coatings of molecularly imprinted particles can be obtained on a surfaces of different supports of interest. FIG. 4 is a schematic drawing of an apparatus used to deposit particles on a substrate surface. A movable stage 28 has a substrate 30 positioned thereon. The coating apparatus 32, which is substantially as described in conjunction with FIG. 1, has a nozzle 34 directed at the movable stage 28. The combination of a propellant assisted coating process, as described in conjunction with FIG. 1, and a moving stage 28, allows for a unique way of controlling the substrate to be coated in a well defined position relative to the nozzle 34 and the formation of precision thin coatings, including thin coatings which can be used on small parts (e.g., the process would allow the creation of a semiconductor chip separation devices wherein a channel could be selectively coated with particles of interest, including those with molecular imprinting having specific selectivity to analyte). Examples 1 and 2 clearly demonstrate compatibility of developed coatings with micro fabricated devices such as SAW devices, while the particle size is smaller than spacing between interdigital electrodes. Other microfabricated devices can be selected from acoustical devices (thickness shear mode(TSM), surface acoustic wave (SAW), acoustic plate mode (APM), flexural plate-wave (FPW)), optical sensing devices, such as surface plasmon resonance (SPR), capacitance, impedance measuring devices. The solute material can be a low or high molecular weight material, used alone or in conjunction with other components.

In the processes described in conjunction with Examples 1, 2, and 5 the movable stage was a rotating platform. Thin coatings of solute were delivered to a SAW surface with very high precision and reproducibility. This was accomplished by adjusting the solute concentration to a low level (in the case of Examples 1, 2, and 5, the solute concentration was below 1 wt % monomer; however, it should be understood that control might be achieved with higher solute concentrations, such as concentrations with below 10–30 wt % monomer), as well the adjustment of offset position (x) between 0.5–5.0 cm. The final morphology of developed coatings can also be different from those achieved by other coating methodologies. It depends on the type of solute and propellant, solute molecular weight, composition of particles, as well as processing conditions. The rotatable platform allows for exact placement of the substrate relative to the spray jet. However, the movable stage 28 could be a conveyor or any other device which can bring the substrate 30 to a precise location below the nozzle 34. Movement below the nozzle can occur a single time or multiple times in repetition until a desired thickness of deposited particles is achieved. The optimization is to be made for type or solute to be delivered, propellant used, and support to be coated. Other factors having impact on the process include pre-expansion pressure, pre-expansion temperature, nozzle inner diameter, nozzle length, nozzle to substrate distance, offset position of the substrate from the nozzle, and the speed of movement of the stage 28. For the SAW devices with DSP and EPA imprinted particles described in conjunction with Examples 1 and 2, the technique allowed for formation of very thin coatings, which were highly reproducible (less than 2–7% standard deviation under various test conditions).

The molecularly imprinted particles of the present invention can have many different applications. For example, they may be incorporated into the filter of a cigarette to selectively bind tar and other unhealthy materials before they are delivered to the lungs of the smoker. They could be incorporated into or deposited on a filter which separates out undesired agents (in the case of, for example, water or air purification), or which serves to collect analytes of interest from a solution under test (e.g., binding enzymes or other materials in a urine or blood sample for diagnosis purposes). The particles can be deposited on substrates such as tubes, flasks, chromatography devices, SAW devices, semiconductor chips, filter media, etc., or they may be unattached to such devices. If the particles are unattached, they can be collected in a container which may be used for chromatography, filtration, purification, etc. The molecularly imprinted polymer particles may be associated with an indicator and serve as a sensor for the detection of the presence or absence of an analyte of interest (although in many sensor applications, the indicator would not need to be present on the sensor). In addition, the imprinted polymer particles might also be used in drug delivery applications such as those described in Example 3.

In addition, in the present invention, imprinted particles can be made using the same propellant based methodologies using compounds other than monomers. The "compounds" can be polymers, proteins, mixture of polymers, mixture of proteins, or combination. For example, there is new concept of molecular imprinting of Nylon-6 polymer with L-glutamine template in the solution. The recognition of amino acids by L-glutamine imprinted-polymer was evaluated by binding experiments for L-glutamine and its analogues and it was revealed that the recognition was effective for L-glutamine by the imprinted polymer as compared with its racemate D-glutamine and L- or D-glutamic acid (Reddy, P. S., T. Kobayashi, et al. (2002). Molecular imprinted Nylon-6 as a recognition material of amino acids. *European Polymer Journal*, 38(3): 521–529). The recognition experiments were extended to membrane filtration and quartz-crystal microbalance response by using the imprinted Nylon-6. Evidence was also presented by FT-IR analysis that the amide hydrogen-bonding interaction between the imprinted Nylon-6 and template was originated for the amino acid recognition (Reddy, P. S., T. Kobayashi, et al. (1999). Molecular imprinting in hydrogen bonding networks of polyamide nylon for recognition of amino acids. *Chemistry Letters*, (4): 293–294).

While much of the above discussion has been devoted to employing the propellant assisted method for molecular imprinting of particles, it should be understood that this method, due to its use of a propellant, has several new and advantageous applications for forming particles of solid state reactivity which are not molecularly imprinted. An important advantage of the particle formation methodology noted above, wherein a monomers of solid state reactivity are expanded into particles of tunable size and shape, is that the particles can be activated immediately or after collection, or at a later time up to 1–10 years and longer. That is, the particles thus produced, whether they contain only solid state reactivity monomers or a mixture of such monomers with other materials, will hold their particulate shape until such time as final polymerization is induced. The particles can be nanoscale, or up to 100 microns in size (for example, 10 nm–100 nm; 10 nm–1 micron; 1–10 microns, etc., are all possible size dimensions of particles formed by the above described methods). As discussed above, the particles formed according to the above processes can be used to uniformly coat the surfaces of various substrates. They can be adhered to a substrate surfaces (e.g., quartz, glass, ceramic, metal, silicon, gallium arsenide, piezoelectric, polymer, etc.) without additional surface agents.

The embodiment for development of small particles with solid state reactivity can be demonstrated referring to the FIG. 1. An important feature of this invention is that monomers or any materials with solid state reactivity can be solubilized in propellant to make mixtures capable of expansion by discharge through a nozzle or orifice 14 into a chamber 16, which should be shielded from the energy source, needed to initiate the reaction in the material. In this way, the propellant is used to make a mixture 10 that can be segregated into many small particles (less than 100 $\mu$m, and less than 1 $\mu$m for some applications) that are emanating from the nozzle or orifice 14. The propellant may contain co-solvent, surfactants, antisolvents, and other chemical constituents. In a preferred embodiment, the propellant may include, for example, chlorofluorocarbons (freons), hydrofluorocarbons, alkanes, alkenes, noble gases (e.g., helium and argon), hydrogen, fluorocarbons, nitrous oxide, ammonia, carbon monoxide and carbon dioxide.

The propellant in this invention could contain at least one supercritical fluid, alone or in combination with a gas or other liquid. In addition, the propellant could include other materials, which will solubilize monomers used in the practice of this invention. The chief requirement is that a uniform distribution of monomers and is achieved with the propellant, and upon discharge through a nozzle 14, the propellant leaves its association in the mixture in a gas form to produce a particle flow 18 in chamber 16, which should be shielded from the energy source, needed to initiate the reaction in the material. Specifically, as the mixture 10 is expanded through the nozzle due to entry of the mixture into a lower pressure environment, all of the gaseous components immediately leave the mixture, leaving only the non-gaseous matrix forming components in the form of small particles. The propellant can be vented from the chamber 16, or, it can be captured and recycled from the chamber 16 to the tank 12 using a pump.

This technique of particle formation, particularly, when supercritical fluids are utilized in the propellant, is based on the tremendous solubility change that occurs during the sudden decompression of a supercritical solution containing a nonvolatile solute by means of an expansion device, such as an orifice or capillary nozzle. The high supersaturation during fluid expansion results in the nucleation and growth of solute particles with mean size ranging from nanometers to tens of microns. The size and morphology of precipitates is controlled by tuning the supercritical solution parameters (concentration of solute, pre-expansion temperature and pressure) as well as the geometry of the expansion device. The propellant may comprise 20–99.99% by weight of the mixture, and the monomers and other constituents may comprise 80–0.01% by weight of the mixture.

The particles developed by this technique also can be collected on the surface of support, such as sensors, data storage media, semiconductors, electronic devices, films, filters.

The invented method of development of small particles, possessing solid state reactivity has several advantages over the currently used technique for handling materials with solid state reactivity. One of the most important advances is the ability to produce non-agglomerated small particles that retain solid state reactivity for a long period of time (e.g., up to 1 or 10 years). The monomer particles can be used alone or in combination with other materials, such as binders, polymers, or mixtures. The particles can be activated at any specific time. There is no impurities in particle composition due to the solvent residue. Particle size can be tailored by choosing experimental conditions, such as concentration of the monomer, pre-expansion pressure and temperature, geometry of the expansion device. Particles can be developed with the same as, or different from bulk monomer properties. (amorphous state of the highly crystalline DSP monomer; higher photoreactivity of the small monomer particles compared to the big crystals)

Example 4 describes a write-once read many times application (optical data storage method) which employs the particles formed by a mixture of solid state reactivity monomers and propellant. This embodiment of the invention is based on preparing a composite material with required components: small particles from a solid photosensitive monomer exhibiting solid state reactivity and polymer matrix; recording information due to exposure to a light source; and developing the image by thermal treatment (heating) optionally followed by final illumination. A write-once read-many-times (WORM) data storage device utilizes small particles of a solid photosensitive monomer exhibiting solid state reactivity that can undergo solid state polymerization under irradiation (by UV, visible, or IR light). Such recording materials have been described in the literature (Nakanishi, F.; Nakanishi H.; Kato, M.; Tawata, M.; Hattori, Shuzo. Dry-process recording material by use of photosensitized solid-state reaction of m-phenylenediacrilic acid. J. Appl. Polym. Sci. 1981, 26 (10) 3505–10).

In this application of the invention, a composition is prepared comprising monomer particles that retain solid state reactivity that are deposited into a polymer matrix. The monomers with the solid state reactivity is preferably selected from the group vinyl stearate, vinyl acetate, isoprene, vinyl octacecyl ether, methacrylic acid, trioxane, diacetylenes, and diolefinic compounds, such as, 2,5-distrylpyrazine (DSP), 2,2'-(2,2-p-phenylene-divinyl)-bis-pyridine, diethyl p-phenylenediacrylate dimethyl p-phenylenediacrylate. The polymer matrix preferably is selected from the group of: polycarbonates, polysiloxanes, and polyesters (however, other polymer matrices may also be empolyed. Any techniques for monomer particles production can be used, including one based on the use of fast expansion of propellant, or recrystallization in the polymer matrix be evaporation of the solvent or changing a temperature.

The polymer matrix is solidified to prevent dimensional changes in the future. The solidification of polymer matrix can be performed by curing, network formation, passing trough liquid-solid transition, evaporation of solvent. The composite material can be optionally passivated to release any stress and prevent future matrix distortion. Then, the formed composite material is selectively exposed to energy source sufficient to polymerize monomer particles and to form a patterned image. Any two-dimensional or three-dimensional image writing technique can be used. The writing technique selectively exposes only a portion of the monomer particles exhibiting solid state reactivity to radiant energy. This causes polymerization of the exposed portion, without polymerization of the unexposed portion.

After that, the composite material comprised of polymer particles, monomer particles, and polymer matrix is subjected to heat at a temperature and for period of time sufficient to cause monomer particles (which did not undergo a solid state reaction) to diffuse into polymer matrix (this is usually for less than 10 minutes, but the time can vary depending on the temperature, choice of materials, etc.). Then, the prepared material can optionally subjected to an energy source (final illumination or heat treatment) for preferably a short period of time to polymerize diffused particles in the matrix, but away from the written image. An advantage of the described method is that thick materials can be prepared that are capable of optical data storage, such as two-dimensional or three dimensional materials.

EXAMPLE 1

2,5-distrylpyrazine (DSP) is a monomer that does not need any external photoinitiator to activate a reaction of polymerization in the solid state under UV-light irradiation. The apparatus we used had a stainless steel vessel with floating piston to keep the mole fraction of the mixture constant and to maintain a constant pressure during the expansion. The maximum working pressure and temperature of the apparatus was 10,000 psi and 250° C., respectively. The expansion nozzle was a fused silica capillary with the inner diameter of 100 $\mu$m and length of 20 mm. The propellant used was chlorodifluoromethane (Freon-22). DSP monomer 0.2 wt % was placed into the vessel first at room temperature. Then the vessel was closed and propellant was charged into the vessel. The vessel was heated to 120° C. and pressurized to 5000 psi. After two hours, the mixture was expanded trough the nozzle into the collection chamber at the pre-expansion conditions: temperature 120° C., pressure 5000 psi. The particles were collected directly onto Surface Acoustic Wave (SAW) transducers of 250 MHz resonant frequency.

Propellant gas was vented from the collection chamber. Then SAW with coatings were exposed to heptane vapors for 10 minutes, and in presence of heptane vapors irradiated by UV light for 15 minutes (using 100 Watt UV lamp, PC-100S, American Ultraviolet Co, providing a spectral range of 325–382 nm at 22 cm distance). After polymerization the particles were flushed with dry nitrogen for 20 minutes to remove template.

A custom-built dynamic flow sensor calibration system was used to evaluate the imprinting effect. The system accommodates two isolated SAW devices (SAW PRO-250 from Microsensor Systems, Inc.): one coated resonator and one uncoated used as a reference device. The temperature of both SAW devices was maintained at 30±0.5° C. Test vapors were generated by means of evaporation using fritted u-shaped spargers filled with liquid analyte and controlled at 10±0.1° C. The flow rates were regulated in a range of 0.1–0.5 L/m in order to control the analyte concentration. Research grade nitrogen was used as a carrier gas and dilutant. The test gas was applied repeatedly to the sampling resonator with a typical duty cycle of 60 seconds followed by purging with dry nitrogen, while the reference SAW resonator was exposed to a pure nitrogen stream with a matching flow rate.

Figure 2:
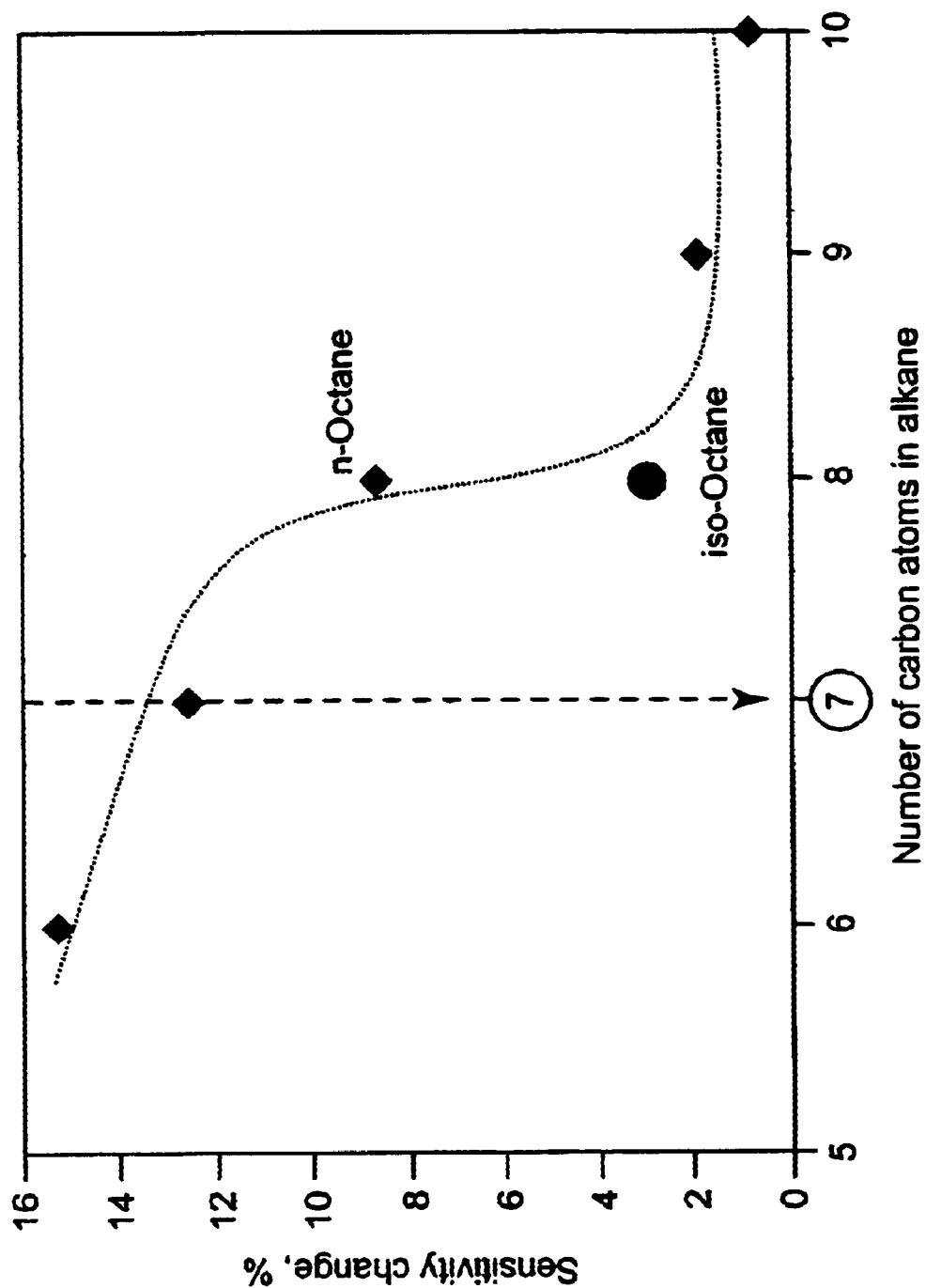
FIG. 2 is a graph showing the change in sensitivity of DSP polymer to alkanes after imprinting by heptane.
Figure 3:
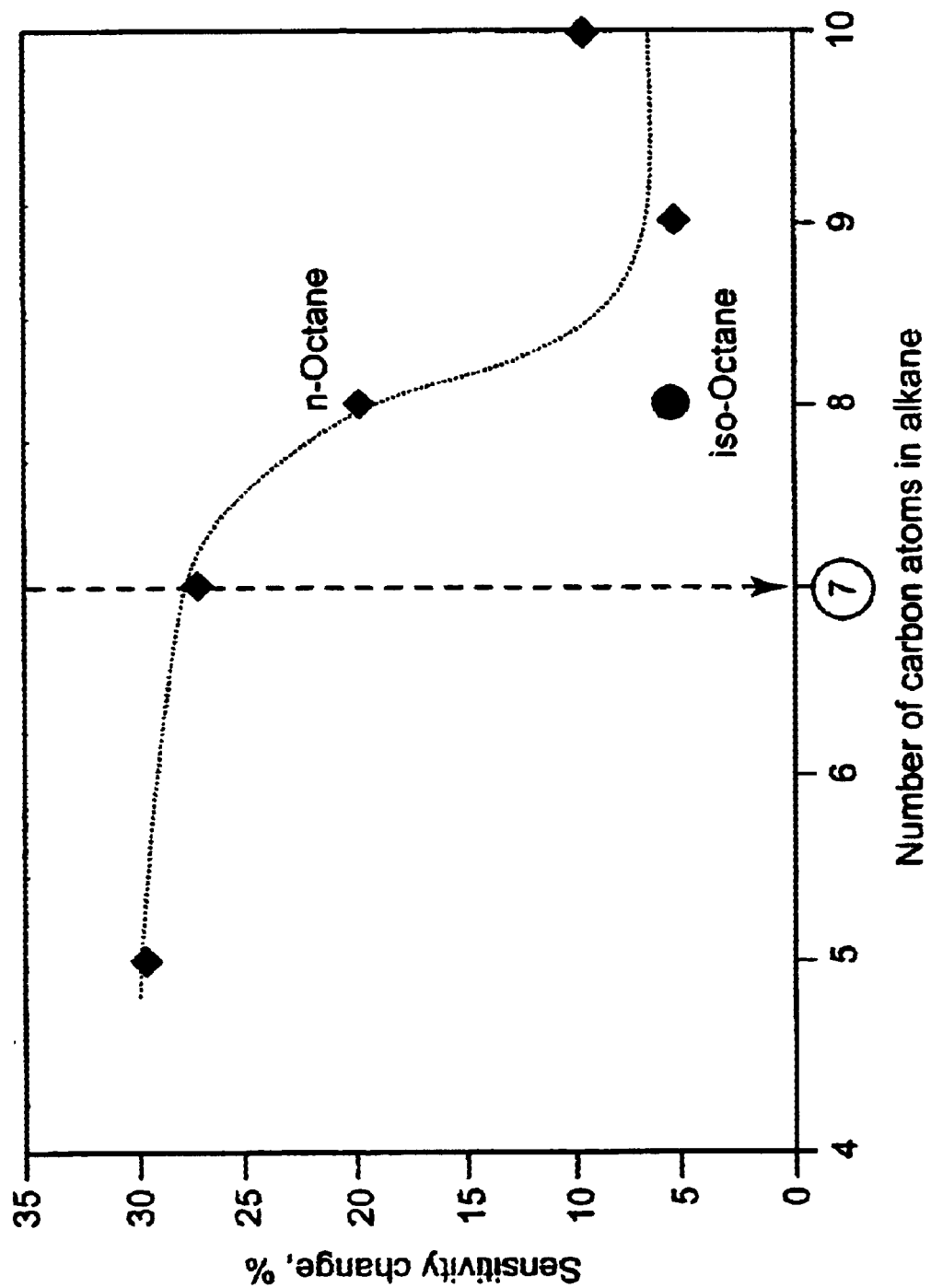
FIG. 3 is a graph showing the change in sensitivity of EPA polymer to alkanes after imprinting by heptane.

The response of SAW transducers coated with the imprinted DSP polymer particles was compared to the response of the SAW device coated with the particles of matching particle size and coating thickness. Analytes used were a family of alkanes with different size of molecular chain, including template, such as pentane, hexane, heptane, octane, nonane, and decane. FIG. 2 shows the change in selectivity of heptane imprinted DSP particles. It can be seen that for n-hexane and n-heptane, the molecularly imprinted polymer particles are significantly more selective than the non-imprinted devices. This selectively rapidly dissipates as the analyte becomes larger (note the decrease for n-octane, n-nonane, and n-decane. Furthermore, FIG. 2 demonstrates that the structure of the analyte plays an important role in selectivity. By comparing the results of iso-octane and n-octane, two compounds of the same carbon make up but of different structure and spatial size, it can be seen that the DSP molecularly imprinted with heptane was not significantly more selective for isooctane than the non-imprinted DSP.

EXAMPLE 2 p-phenylenediacrylate (EPA) is a monomer capable of polymerization in the solid state. The apparatus was the same as described in the Example 1. The expansion nozzle was a fused silica capillary with the inner diameter of 100 µm and length of 20 mm. The propellant used was chlorodifluoromethane (Freon-22). EPA monomer 0.07 wt % was placed into the vessel first at room temperature. Then vessel was closed and propellant was charged into the vessel. The vessel was heated to 120° C. and pressurized to 5000 psi. After two hours, the mixture was expanded through the nozzle into the collection chamber at the pre-expansion conditions: temperature 130° C., pressure 5000 psi. The particles were collected directly onto a SAW transducers of 250 MHz resonant frequency. Propellant gas was vented from the collection chamber. Then SAW with coatings were exposed to heptane vapors for 10 minutes, and, in the presence of heptane vapors irradiated by UV light for 15 minutes (using 100 Watt UV lamp, PC-100S, American Ultraviolet Co, providing a spectral range of 325–382 nm at 22 cm distance). After polymerization, the particles were flushed with dry nitrogen for 20 minutes to remove template.

FIG. 3 shows the change in selectivity of heptane imprinted EPA particles. It can be seen that for n-hexane and n-heptane, the molecularly imprinted polymer particles are significantly more selective than the non-imprinted devices. This selectively rapidly dissipates as the analyte becomes larger (note the decrease for n-octane, n-nonane, and n-decane. Furthermore, FIG. 3 demonstrates that the structure of the analyte plays an important role in selectivity. By comparing the results of iso-octane and n-octane, two compounds of the carbon make up but of different spatial size and structure, it can be seen that the EPA molecularly imprinted with heptane was not significantly more selective for isooctane than the non-imprinted EPA.

EXAMPLE 3

Enzymes perform a key role in living organisms, catalyzing the transformation of substrates to specific products. In general, enzymes are proteins (polypeptides) of varying size and amino acid residue composition. Each enzyme is designed to catalyze a specific reaction. The high reaction rate and the selectivity of the reaction are two characteristics of the enzyme-catalyzed reactions. The preparation of materials possessing enzymatic behavior is useful to catalyze the reaction of industrial interest, especially in reactions for which no natural enzyme is available. One of the key features of a natural enzymatic process, apart from the high rate of reaction, is selectivity. The selectivity of enzymes is highlighted by the following:

1) Enzymes are able to direct the chemical reaction to one specific part of the substrate, e.g. an enzyme may catalyze a chemical reaction at one specific site on the substrate while leaving other sites unaffected. These may be equally liable to reaction when performing the reaction by chemical means.

2) Enzymes are selective for their substrates. Enzymes can operate in a mixture of compounds, but bind and act upon only one (the substrate) or a few of the components of the mixture.

3) Enzymes are selective with respect to the chemical reaction performed. One substrate may undergo a variety of chemical conversions, each catalyzed by a specific enzyme.

4) Enzymes can perform their chemical reactions selectively with respect to the stereostructure of the substrate and product. Only one enantiomeric form of a substrate can be converted or from a prochiral substrate (i.e., only one enantiomeric form of the product is produced).

All of these types of selectivity of enzyme catalysis are attractive for the chemist to mimic in the construction of synthetic enzymes by molecular imprinting technique. In contrast to the enzymes, antibodies are capable to bind selectively to antigens. The formed antibody-antigen complex, is also a subjected of further conversions. The preparation of synthetic enzymes is well recognized and includes the synthesis of compounds based on natural starting material (cyclodextrin) (R. Breslow, A. W. Czarnik, J. Am. Chem. Soc. 105,1390 (1983)) and the preparation of fully synthetic systems (J-M. Lehn, C. Sirlin, J. Chem. Soc. Chem. Commun., 949,(1978) and D. J. Cram, P. Y. Lam, S. P. Ho, J. Am. Chem. Soc, 108, 839 (1986)). U.S. patents describing molecular imprinting used for development of artificial enzymes are U.S. Pat. No. 5,110,833 Mosbach and U.S. Pat. No. 5,801,221, Tanaka, et al., each of which have been incorporated herein by reference.

While not previously recognized, imprinting of nanoparticles can be very useful for drug targeting as well. Nanoparticles are solid, colloidal particles consisting of macromolecular substances that vary in size from 10 nanometers (nm) to 1000 nm. In this embodiment of the invention, the drug is dissolved, entrapped, adsorbed, attached, or encapsulated in the macromolecular material(s). Choosing the appropriate polymer, particle size, and method of production would depend on three major aspects: bioacceptability of the polymer, physicochemical properties of the drug, and the type of therapy the drug should have. The use of polymers for nanoparticles is usually restricted by their bioacceptability. The bioacceptability is affected by the polymer and the supplementary components, as well as by particle size (Microparticulate systems for the delivery of proteins and vaccines. Ed. S. Cohen, H. Bernstein, 1996, Drugs and Pharmaceutical Sciences, 77 ). A reduction in the particle size of the polymeric particles has many advantages, which are listed below.

1.) Intravenous injection can be allowed if there is a decrease in the particle size.

2.) Intramuscular and subcutaneous distribution require small particle size.

3.) Irritant reactions at the injection site are minimized by using small particle size.

4.) Carcinogenic effects depend on particle size.

Some important practices for which nanoparticles are used include the adsorbing and coating of organs and tissues, peroral administration of drugs, vaccinations, the delivery of anti- inflammatory drugs, and the delivery of drugs for diseases and tumors. Significant efforts in this field are now focused on the surface modifications of the nanoparticulate drug carriers in order to improve their targeting properties. Therefore molecular imprinting of drug carriers can improve the interactions with specific epithelial cells to target specific sites. This invention, therefore, particularly contemplates a molecularly imprinted particle with an active agent (e.g., drug in the case of a therapeutic agent; toxin or oxidizing agent in the case of a cancer treatment, etc.) associated with the particle. The particle would be imprinted with a target molecule (e.g., enzyme, etc.) or substrate (cell, DNA, RNA, etc.) which would allow the particle to bind to the biological material of interest, and would then deliver the active agent at the targeted site. This can occur by dissolution of the polymer particle with subsequent release of the active agent, or by the active agent present on the surface of the polymer particle being free to take its intended action, or by other means. In contrast to the enzymes, antibodies are capable to bind selectively to antigens. According to the present invention, the synthetic antibody would be developed as the imprinted particle capable of the template specific binding, for example to specific antigen. While the particle (synthetic antibody) is bound to the site of interest, it can stay at the site certain time. The imprinted particle (synthetic antibody) may include other chemical/biological compounds, which are not needed for molecular imprinting, but can be incorporated into the molecularly imprinted particle. When such prepared "loaded" synthetic antibody binds to the template specific site, the "load" can be released from the particle. The load to artificial antibodies can be selected from drug, neurotransmitters hormone, or the other biologically active compounds or catalyst. Released load is administrated to the area of the antigen-antibody complex in order to make changes to the living organism. This can occur by dissolution of the polymer particle with subsequent release of the active agent, or by the active agent present on the surface of the polymer particle being free to take its intended action, or by other means.

EXAMPLE 4

This embodiment of the invention is based on preparing a composite material with required components: small particles from a solid photosensitive monomer exhibiting solid state reactivity and polymer matrix; recording information due to exposure to a light source; and developing the image by thermal treatment (heating) optionally followed by final illumination.

Step 1. Preparing a composite material

A write-once read-many-times (WORM) data storage device utilizes small particles of a solid photosensitive monomer exhibiting solid state reactivity that can undergo solid state polymerization under irradiation (by UV, visible, or IR light). Such recording materials have been described in literature (Nakanishi, F.; Nakanishi H.; Kato, M.; Tawata, M.; Hattori, Shuzo. Dry-process recording material by use of photosensitized solid-state reaction of m-phenylenediacrilic acid. J. Appl. Polym. Sci. 1981, 26 (10) 3505–10). The small particles of the monomer are embedded in a polymer matrix and can diffuse into the polymer matrix under heat treatment. The polymer for the matrix must be transparent to the light used as the writing source, thermostable, and mechanically stable (i.e. does not change dimensions after thermal treatment and over time during storage).

Form a data storage media from the composition of a photosensitive monomer possessing solid state reactivity and a polymer matrix by any suitable technique (Examples include: injection molding, coating techniques etc.). Solidify the polymer matrix by curing, network formation, or passing through liquid-solid transition. Optionally passivate the resultant composite material to prevent further dimensional changes that can cause image distortion. Any technique for monomer particles production can be used. We used 2,5-distyrylpyrazine (DSP) 100 nm particles produced by the fast expansion of propellant, as described in the present invention. Particularly, clorodifluoromethane (99.8 wt %) was used as a propellant. The mixture was expanded through the nozzle into the collection chamber at the pre-expansion conditions: temperature 120° C., pressure 5000 psi. The collected chamber was made to prevent light from entering. The particles are collected on the surface of support (glass microscope slides) to form a coating consisting from small particles. As an example of a polymer matrix we used polydimethylsiloxane methyldiacetoxy terminated (PDMSMA) CAS #70879-95-7. Polymer was cast over the coating of DSP particles and a layer from the DSP-PDMSMA mixture having thickness of 0.7 mm was prepared in the dark environment. Then the polymer matrix was cured in a dark environment by water vapor and the resultant composite material was passivated at 40° C. for 30 minutes to prevent further dimensional changes that can cause image distortion.

For two-dimensional images sometimes the use of polymer matrix can be optional. We developed a dry-process recording material from DSP 100 nm particles without use of polymer matrix. The image was created according to the step 2, without need of polymer matrix curing. After image development by short heating (step 3), the image is stable and ready for readout of information. Thus, polymer matrix optionally can be avoided for some cases, for thin coatings for example.

Step 2. Recording the information

Write the information to be stored (2-D or 3-D) by means of a light source device (laser, for example), that induces the solid state reaction in the monomer particles. We used, for example, UV laser with 365 nm wavelength and 100 Watt UV lamp, providing a spectral range of 325–382 nm. Where exposed, the DSP monomer particles undergo solid state polymerization under irradiation by UV light, resulting in the formation of a high molecular weight polymer structure. We recorded two-dimensional images using physical mask to form a patterned image. One can understand that any known methods of recording of optical information can be employed.

Step 3. Image Development

Generally, to prevent image smearing (damage) in the presence of any future irradiation during data readout or storage an additional step—image development is needed. We introduced a short thermal treatment as an image development technique. We heated the data storage device consisting of DSP—PDMSMA composite layer having thickness of 0.7 mm with recorded information to a temperature of 200° C. for 2–5 minutes. The unreacted DSP monomer, diffuses into the polymer matrix during heating, while reacted DSP polymer developed during information recording does not. The difference in diffusion and vapor pressure between the reacted and unreacted material provides the image preservation. The image is clearly seen after that. After the development step the data storage device is stable and ready for readout of information. In some cases it may be necessary to illuminate material to fix the unreacted particles in the polymer matrix away from the image.

This embodiment of the invention provided a method whereby a two dimensional or three dimensional image may be stored for later use. The solid photosensitive particles produced according to the described technique need only be combined with a polymer matrix to preserve a spacious structure of the layer of particles. The image is then created by a writing source such as laser light directed at the particles, which causes the imaged particles to polymerize, with a fast thermal treatment to develop the image. That is, the difference between reacted particles (those exposed during radiation) and unreacted particles (those not exposed) in diffusing into the polymer matrix fully develops the image. Thus optical storage is obtained by a three step process whereby 1) particles are developed by the fast expansion of propellant and mixed with/without polymer matrix, 2) a precise writing tool directs energy at the coated polymer matrix to selectively form two dimensional or three dimensional structures by selectively polymerizing the monomer particles thereon, and 3) developing by a simple heat treatment to fix the image by a difference in diffusion properties between reacted and unreacted particles. The described materials for storing optical data are advantageous over the prior art as having greater physical thickness of the composite layer, up to 1 mm, and up to 5 mm in some cases with small particles. This is important for three dimensional images such as holography.

EXAMPLE 5

The methods used in Examples 1 and 2, and described above in conjunction with FIG. 4 illustrate methodologies whereby thin uniform thickness coatings are formed from low and high molecular weight substances, consisting of particulate morphologies or uniform films, chemically/mechanically adhered to the surfaces. Surfaces to be coated can be conductive, non-conductive, semiconductive (e.g., silicon or gallium arsenide), piezoelectric, magnetic or non-magnetic, quartz, glass, metal, polymer, ceramic, zinc oxide, lithium neobate, etc. In addition, the substrate could be porous or non-porous.

Figure 4:
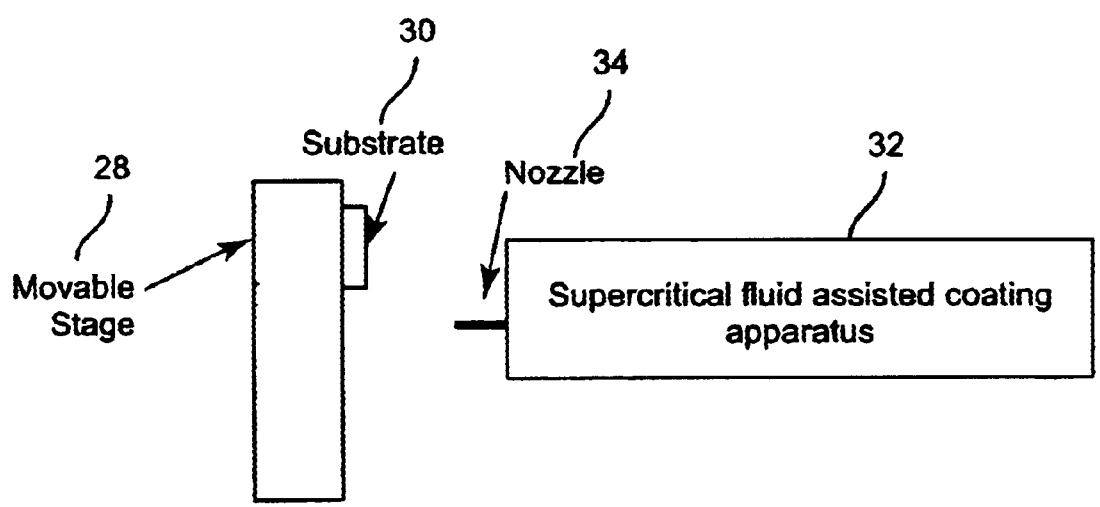
FIG. 4 is a schematic diagram of a system for depositing thin coatings of particles on substrates which employs a movable stage.
Figure 5:
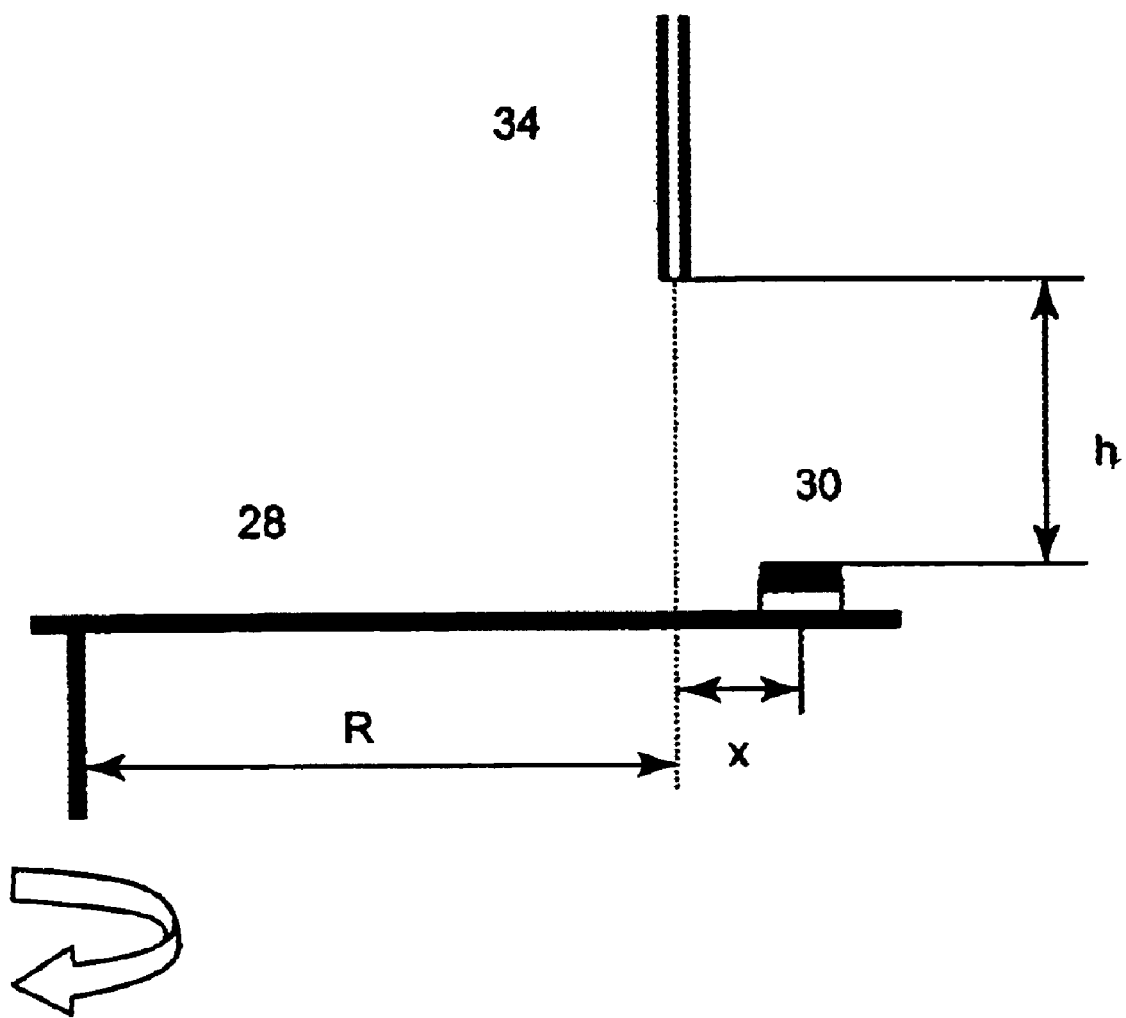
FIG. 5 is a schematic diagram showing the relationship of the nozzle in FIG. 4 to the substrate.

FIG. 5 shows a schematic diagram of the nozzle region that pertains to the system shown in FIG. 4. In FIG. 5, the moveable stage 28 holds one or more substrates 30 a distance h below the nozzle 34. The offset x represents the distance the substrate 30 is positioned from direct alignment with an outlet of the nozzle 34. The radius R represents the radius from the center of rotation to the center of the spray from nozzle 34. In one experiment where polymer was deposited over a SAW device with 250 MHz resonant frequency, the copolymer 50% methylphenyl-50% diphenyl siloxane was deposited from chlorodifluoromethane to result in coating thickness of 350 kHz at conditions as follow: solute concentration—0.11 wt %; offset (x)—1.0 cm; nozzle-to-substrate distance (h)—2.5 cm; rotation speed—4.12 rpm; radius from the center of rotation to the imaginable center of the spray (R)—6.0 cm; pre-expansion temperature—125 C; pre-expansion pressure—5000 psi. In another experiment pertaining to monomer deposition over the SAW devices with 250 MHz resonant frequency, the 2,5-distyrylpyrazine (DSP) monomer was deposited from chlorodifluoromethane to result in coating thickness of 90 kHz at conditions as follows: solute concentration—0.15 wt %; offset (x)—0.8 cm; nozzle-to-substrate distance (h)—2.0 cm; rotation speed—5.23 rpm; radius from the center of rotation to the imaginable center of the spray (R)—6.0 cm; pre-expansion temperature—130 C; pre-expansion pressure—5000 psi.

For the SAW devices with 250 MHz resonant frequency coated with monomer and polymer particles described in conjunction with Examples 1 and 2, the acoustical thickness, expressed as a frequency shift of 250 MHz resonant frequency device, can vary from 90 to 1,000 kHz.

The offset serves an important function in that it allows thin coatings of solute (e.g., monomers, polymers, etc.) to be created without microscopic defects due to physical impaction of the stream on the substrate surface.

While the invention has been described in conjunction with its preferred embodiments, those of skill in the art will recognize that the invention can be practiced with considerable variation within the spirit and scope of the appended claims.

We claim:

1. A method of molecular imprinting of polymer materials, comprising the steps of:
   expanding a mixture containing a propellant and monomers to form particles;
   introducing a template into said particles which is selectively releasable from a polymer formed from said monomers in said particles;
   polymerizing said particles in the presence of said template to form composite particles having polymer and template, wherein said template is not bound to said polymer; and
   extracting said template from said composite particles without distorting a morphology of said composite particles to provide polymerized particles imprinted by said template with a size and arrangement of chemical functional groups complementary to said template.

2. The method of claim 1 wherein said introducing step is performed by combining said template with said mixture prior to said expanding step.

3. The method of claim 2 wherein said propellant dissolves said monomers and said template to form a homogenous mixture.

4. The method of claim 1 wherein said introducing step is performed by combining said template with said mixture after said expanding step.

5. The method of claim 4 wherein combining is performed by diffusing said template from a gas phase into said particles.

6. The method of claim 1 wherein said mixture further comprises a photoinitiator.

7. The method of claim 1 wherein said mixture further comprises a crosslinking agent.

8. The method of claim 1 wherein said polymerizing step is performed in an initial and a final polymerization,
   wherein in said initial polymerization, said particles are subjected to energy selected from the group consisting of heat and radiant energy in an amount sufficient to initiate polymerization of said monomers, and
   wherein in said final polymerization, said particles are subjected to energy selected from the group consisting of heat and radiant energy in an amount sufficient to fully polymerize said monomers.

9. The method of claim 8 wherein said energy used in said initial polymerization and said final polymerization can be the same or different, and is selected from the group consisting of heat, ultraviolet, gamma, and infrared radiation.

10. The method of claim 9 wherein said energy used in said initial polymerization and said final polymerization are both ultraviolet radiation.

11. The method of claim 8 wherein said expanding step creates said particles from said mixture in a gaseous environment, and wherein said initial polymerization is performed by subjecting said particles to said energy in said gaseous environment.

12. The method of claim 11 wherein said gaseous environment is inert.

13. The method of claim 12 wherein said gaseous environment is nitrogen.

14. The method of claim 11 wherein said gaseous environment includes air.

15. The method of claim 11 wherein said final polymerization is performed by subjecting said composite particles to said energy after said composite particles are collected on a substrate.

16. The method of claim 1 wherein said polymerizing step is performed by subjecting said particles to an energy source selected from the group consisting of heat and radiant energy.

17. The method of claim 1 wherein said monomers have solid state reactivity.

18. The method of claim 17 wherein said monomers are selected from the group consisting of vinyl stearate, vinyl acetate, isoprene, vinyl octacecyl ether, methacrylic acid, trioxane, 2,5-distrylpyrazine, 2,2'-(2,2-p-phenylenedivinyl)-bis-pyridine, diethyl p-phenylenediacrylate, dimethyl p-phenylenediacrylate, diolefinic compounds and diacetylenes.

19. The method of claim 1 wherein said monomers are the same.

20. The method of claim 1 wherein said monomers include at least two different chemical moieties.

21. The method of claim 1 wherein said monomers are selected from the group consisting of acrylic acids, acrylamides, vinylbenzoic acids, acrylamino-sulfonic acids, amino-metacrylamides, vinylpyridines, vinylimidazoles, vinyl-iminodiacetic acids, etherketones, and etheretherketones.

22. The method of claim 1 wherein said propellant includes at least one compound selected from the group consisting of chlorofluorocarbons, hydrofluorocarbons, alkanes, alkenes, noble gases, nitrogen, sulfur hexafluoride, fluorocarbons, nitrous oxide, hydrogen, ammonia, carbon monoxide and carbon dioxide.

23. The method of claim 1 wherein said template is a chemical compound having a molecular weight ranging from 10 to 1,000,000.

24. The method of claim 1 wherein said template is a biological compound or substrate.

25. The method of claim 1 wherein the propellant includes as at least one component a supercritical fluid.

26. The method of claim 25 wherein said supercritical fluid solubilizes said monomers in said mixture.

27. The method of claim 1 wherein said particles formed in said expanding step are less than one micron in size.

28. The method of claim 1 wherein said particles formed in said expanding step are a liquid.

29. The method of claim 1 wherein said particles formed in said expanding step are a solid.

30. The method of claim 1 wherein said template introduced in said introducing step does not covalently bond to said monomers.

31. A method for coating a substrate surface with particles, comprising the steps of:
    expanding a mixture containing a propellant and monomers to form a particle stream;
    depositing particles on a substrate surface by directing said particle stream at said substrate surface, said depositing step being performed in a manner whereby said particles retain a morphology developed from said expanding step; and
    polymerizing said particles on said substrate surface, wherein said polymerizing step adheres said particles to said substrate surface.

32. The method of claim 31 wherein said depositing step includes the step of periodically moving said substrate surface in and out of said particle stream.

33. The method of claim 31 wherein said polymerizing step is performed by exposing said particles to radiant energy.

34. The method of claim 31 wherein said polymerizing step is performed by exposing said particles to thermal energy.

35. The method of claim 31 further comprising the steps of:
    introducing a template into said particles prior to said polymerizing step which does not covalently bind to said monomers; and
    extracting said template from said particles after said polymerizing step without distorting a morphology of said particles to provide polymerized particles imprinted by said template with a size and arrangement of chemical functional groups complementary to said template.

36. The method of claim 31 wherein said depositing step produces a layer of said particles which does not exceed 1 micron thick.

37. A method for storing optical information, comprising the steps of:
    forming a composition comprising particles formed from a monomer of solid state reactivity and a polymer matrix;
    selectively exposing a portion of said particles to energy sufficient to polymerize said monomers of solid state reactivity in said portion; and
    heating said particles at a temperature sufficient to cause particles not exposed in said selectively exposing step to diffuse into said polymer matrix.

38. The method of claim 37 wherein said polymer matrix is selected from the group consisting of polycarbonates, polysiloxanes, and polyesters.

39. The method of claim 37 wherein said selectively exposing step polymerizes particles in a manner which creates a two dimensional image.

40. The method of claim 37 wherein said selectively exposing step polymerizes particles in a manner which creates a three dimensional image.

41. The method of claim 37 wherein said monomers of solid state reactivity are selected from the group consisting of consisting of vinyl stearate, vinyl acetate, isoprene, vinyl octacecyl ether, methacrylic acid, trioxane, 2,5-distrylpyrazine, 2,2'-(2,2-p-phenylene-divinyl)-bis-pyridine, diethyl p-phenylenediacrylate, dimethyl p-phenylenediacrylate, diolephenic compounds and diacetylenes.

42. A method for storing optical information, comprising the steps of:
    forming a composition comprising particles formed from monomer of solid state reactivity and a polymer matrix; wherein said forming step includes the step of expanding a mixture containing a propellant and said monomers of solid state reactivity into said polymer matrix;
    selectively exposing a portion of said particles to energy sufficient to polymerize said monomers of solid state reactivity in said portion; and
    heating said particles at a temperature sufficient to cause particles not exposed in said selectively exposing step to diffuse into said polymer matrix.

43. A method for preparing a material for selectively joining with an analyte, comprising the steps of:
    expanding a mixture containing a propellant and monomers to form particles;
    introducing a template into said particles which is selectively releasable from a polymer formed from said monomers in said mixture and wherein said template is different from said analyte;
    polymerizing said particles in the presence of said template to form composite particles having polymer and template; and
    extracting said template from said composite particles without distorting a morphology of said composite particles to provide polymerized particles imprinted by said template.

44. A method of molecular imprinting of particles, comprising the steps of:
    expanding a mixture containing a propellant and at least one compound which can conform to a molecular configuration of a template to create particles;

introducing a template into said particles which is selectively releasable from said compound in said particles;

solidifying said compound in said particles with said template positioned therein; and extracting said template from said particles without distorting a morphology of said particles to provide molecularly imprinted particles.

45. The method of claim 44 wherein said compound is a polymer.

46. The method of claim 44 wherein said compound is a monomer.

47. The method of claim 44 wherein said compound is a biological substance.

48. The method of claim 44 wherein said solidifying step is performed by exposing said particles to a sufficient amount of energy so as to solidify said compound in said particles.

49. A method for coating a substrate with a thin coating, comprising the steps of:

solubilizing a solute with a propellant containing at least on supercritical fluid;

expanding a mixture of said propellant and solute to form a article stream;

depositing particles from said particle stream uniformly on substrate surface by directing said particle stream at the substrate surface from an offset position, to provide a thin coating of uniform thickness of less than 1 micron.

50. The method for coating recited in claim 49, wherein said offset position ranges from 0.5 to 5.0 cm.

51. The method for coating recited in claim 49 wherein said particles are liquid.

52. The method for coating recited in claim 49 wherein said particles are solid.

53. The method for coating recited in claim 49 wherein the concentration of solute in said mixture of propellant and solute is 1 wt % or less.

54. The method of claim 49, wherein the supercritical fluid is a gas after expansion, during particles deposition.

* * * * *